(12) United States Patent
Chen et al.

(10) Patent No.: US 11,877,749 B2
(45) Date of Patent: Jan. 23, 2024

(54) KNOB ASSEMBLY AND CIRCULAR STAPLER

(71) Applicant: TOUCHSTONE INTERNATIONAL MEDICAL SCIENCE CO., LTD., Jiangsu (CN)

(72) Inventors: Zhi Chen, Jiangsu (CN); Yi Guo, Jiangsu (CN); Jiang Lin, Jiangsu (CN)

(73) Assignee: TOUCHSTONE INTERNATIONAL MEDICAL SCIENCE CO., LTD., Jiangsu (CN)

( * ) Notice: Subject to any disclaimer, the term of this patent is extended or adjusted under 35 U.S.C. 154(b) by 306 days.

(21) Appl. No.: 17/298,876

(22) PCT Filed: Dec. 18, 2019

(86) PCT No.: PCT/CN2019/126297
§ 371 (c)(1),
(2) Date: Jun. 1, 2021

(87) PCT Pub. No.: WO2020/125676
PCT Pub. Date: Jun. 25, 2020

(65) Prior Publication Data
US 2022/0054135 A1 Feb. 24, 2022

(30) Foreign Application Priority Data

Dec. 18, 2018 (CN) .......................... 201811549388.5
Dec. 18, 2018 (CN) .......................... 201822131322.6

(51) Int. Cl.
*A61B 17/064* (2006.01)
*A61B 17/115* (2006.01)
(Continued)

(52) U.S. Cl.
CPC ... *A61B 17/1155* (2013.01); *A61B 2017/0042* (2013.01); *A61B 2017/00389* (2013.01);
(Continued)

(58) Field of Classification Search
CPC .................. A61B 17/1155; A61B 2017/00389
See application file for complete search history.

(56) References Cited

U.S. PATENT DOCUMENTS

| 5,497,682 | A | 3/1996 | Hsu |
| 2014/0276893 | A1 | 9/2014 | Schaller et al. |
| 2022/0395274 | A1* | 12/2022 | Fox .................. A61B 17/07207 |

FOREIGN PATENT DOCUMENTS

| CN | 1923151 A | 3/2007 |
| CN | 204814027 U * | 12/2015 |
(Continued)

OTHER PUBLICATIONS

Office Action regarding corresponding JP App. No. 2021-535004; dated Jan. 24, 2023.
(Continued)

*Primary Examiner* — Eyamindae C Jallow
(74) *Attorney, Agent, or Firm* — Dickinson Wright PLLC

(57) ABSTRACT

A knob assembly and a circular stapler are provided. The knob assembly includes a knob driver, a knob body, a first cooperating component and a second cooperating component. In a blocking state, the first cooperating component is linked with the second cooperating component; while in an unblocking state, the first cooperating component is not fixedly linked with the second cooperating component. One of the first cooperating component and the second cooperating component is provided at the knob driver and the other one is provided at the knob body. When the knob driver is rotated, if a rotating resistance to the knob body reaches a preset resistance value, the knob assembly cannot transmit larger torque, therefore the knob assembly is in a failure mode, the position of the anvil assembly relative to the cartridge remains unchanged, and the tissues will not be excessively compressed.

17 Claims, 13 Drawing Sheets

(51) Int. Cl.
*A61B 17/00* (2006.01)
*A61B 17/072* (2006.01)

(52) U.S. Cl.
CPC ............... *A61B 2017/07257* (2013.01); *A61B 2017/07271* (2013.01)

(56) References Cited

FOREIGN PATENT DOCUMENTS

| | | | |
|---|---|---|---|
| CN | 204814027 U | 12/2015 | |
| CN | 105250006 A | 1/2016 | |
| CN | 107708579 A | 2/2018 | |
| CN | 209499811 U | 10/2019 | |
| CN | 111329547 A * | 6/2020 | |
| CN | 217219104 U * | 8/2022 | ......... A61B 17/1155 |
| EP | 2086423 A2 | 8/2009 | |
| EP | 2517650 A2 | 10/2012 | |
| EP | 2965647 A1 | 1/2016 | |
| EP | 3108823 A2 | 12/2016 | |
| EP | 2086423 B1 | 12/2017 | |
| EP | 3461430 A1 | 4/2019 | |
| JP | 5149817 A | 4/1976 | |
| JP | S51-049817 Y1 | 12/1976 | |
| JP | H05228100 A | 9/1993 | |
| JP | 2005257714 A | 9/2005 | |
| JP | 2007050486 A | 3/2007 | |
| JP | 2007068550 A | 3/2007 | |
| JP | 2008133695 A | 6/2008 | |
| JP | 2010504806 A | 2/2010 | |
| JP | 2012232110 A | 11/2012 | |
| JP | 2015503950 A | 2/2015 | |
| JP | 2018519065 A | 7/2018 | |
| WO | 2008042045 A2 | 4/2008 | |

OTHER PUBLICATIONS

Extended European Search Report regarding corresponding EP App. No. 19899353.7; dated Jan. 13, 2022.
First Office Action regarding corresponding CA App. No. 3,121,951; dated Sep. 15, 2022.
First Office Action regarding corresponding JP App. No. 2021-535004; dated Jul. 4, 2022.
First Office Action regarding corresponding KR App. No. 10-2021-7019850; dated Apr. 25, 2023.

* cited by examiner

KNOB ASSEMBLY AND CIRCULAR STAPLER

CROSS-REFERENCE TO RELATED APPLICATIONS

This application is based upon PCT Patent Application No. PCT/CN2019/126297 filed on Dec. 18, 2019, which claims priority to Chinese Patent Applications No. 201822131322.6 and No. 201811549388.5, filed on Dec. 18, 2018, the entire contents of which are incorporated herein by reference.

TECHNICAL FIELD

The present disclosure relates to medical instruments technology, more particularly, to a knob assembly and a circular stapler.

BACKGROUND

Digestive tract disease is one of human diseases of high incidence. During treatment a circular stapler is widely used for suturing physiological tissues such as tissues in the digestive tract, instead of the manual operation by doctors. The circular stapler is a common surgical instrument, and used for end-to-end anastomosis, or end-to-side anastomosis of the physiological tissues of esophagus, stomach, intestine, etc., in a way of axial internal stapling. During the process of anastomoses, two sections of tissues are accommodated in the stapler, and form a circular anastomotic stoma after firing the stapler, to rebuild a tissue channel.

In the prior art, the circular stapler includes an instrument body, a handle assembly movably connected to the instrument body and an anvil assembly cooperated with the instrument body. The instrument body includes a cartridge assembly located at a distal end and a knob located at a proximal end thereof. The cartridge assembly includes a circular cartridge and a cutter, and the knob can be rotated relative to the instrument body. In the present disclosure, positions of the distal end and the proximal end are defined relative to an operator, wherein, the proximal end is an end closer to the operator, the distal end is another end far from the operator and closer to a surgical position. The anvil assembly includes an anvil, an anvil cap at the top of the anvil, a cutter anvil inside the anvil and an anvil shaft detachably connected to the instrument body. During the process of operation, after the tumor tissues are separated and removed, the anvil shaft is connected to the distal end of instrument body through a purse at one end of the tissues, the knob is rotated to drive the anvil assembly to move close to the cartridge. The stapler is then able to be fired by pressing the handle to accomplish the suturing operation. Along with the development of medical instruments, the circular stapler has been more and more widely used for treatment of diseases such as hemorrhoids.

During the process of rotating the knob to move the anvil assembly towards the cartridge, sometimes even after the anvil assembly reached an appropriate position relative to the cartridge, the knob can still be rotated to make the anvil assembly continue to move towards the cartridge, and the anvil assembly and the cartridge will continue to compress the tissues in between. This will cause an excessive compression to the tissues, and may even crush the tissues, which is very unfavorable for the operation effect.

SUMMARY

To solve the problems in the prior art, the present disclosure provides a knob assembly and a stapler, and the knob assembly includes a knob body and a knob driver. When the knob driver is rotated, if a rotating resistance to the knob body reaches a preset resistance value, the knob assembly cannot transmit larger torque, so the knob assembly is in a failure mode. Therefore, the position of the anvil assembly relative to the cartridge remains unchanged, and the tissues will not be excessively compressed.

In the present disclosure, a knob assembly used for a circular stapler is provided, the knob assembly is used for a circular stapler, a screw rod is provided in the stapler, and the knob assembly includes: a knob driver; a knob body sheathed outside the screw rod, wherein when the knob body rotates, the screw rod is driven to move along an axial direction of the stapler; a first cooperating component having a blocking state and an unblocking state, wherein the first cooperating component is an elastic cooperating component; a second cooperating component; wherein when the first cooperating component is in the blocking state, the first cooperating component and the second cooperating component are fixedly linked with each other, when the first cooperating component is in the receding state, the first cooperating component and the second cooperating component are not fixedly linked with each other; wherein the first cooperating component is provided at the knob driver, and the second cooperating component is provided at the knob body; or the first cooperating component is provided at the knob body, and the second cooperating component is provided at the knob driver.

In some embodiments, the knob driver is capable of being rotated by an external force; when a rotating resistance to the knob body is larger than a preset resistance value, the first cooperating component is deformed by a force of the second cooperating component and enters the receding state.

In some embodiments, the first cooperating component is an elastic sheet having a protruding portion.

In some embodiments, the knob driver or the knob body is provided with mounting grooves for the elastic sheet, two ends of the elastic sheet are correspondingly mounted in the mounting grooves for the elastic sheet.

In some embodiments, the elastic sheet includes a first guiding surface; when the knob driver rotates towards a first direction, the first guiding surface of the first cooperating component is in contact with the second cooperating component.

In some embodiments, the first guiding surface is an arc surface or an inclined surface.

In some embodiments, the elastic sheet includes a second guiding surface; when the knob driver rotates towards a second direction, the second guiding surface of the first cooperating component is in contact with the second cooperating component.

In some embodiments, the second guiding surface is an arc surface or an inclined surface.

In some embodiments, the second cooperating component includes at least one cooperating unit, each cooperating unit is a bulge or a groove.

In some embodiments, each cooperating unit includes a first side surface inclined towards a first direction; when the knob driver rotates towards a first direction, the first side surface of the cooperating unit is in contact with the first cooperating component.

In some embodiments, each cooperating unit includes a second side surface; when the knob driver rotates towards a second direction, the second side surface of the cooperating unit is in contact with the first cooperating component.

In some embodiments, the second side surface of the cooperating unit is a vertical surface; or the second side surface of the cooperating unit inclines towards a second direction with an inclined angle smaller than an inclined angle of the first side surface of the cooperating unit.

In some embodiments, the knob driver includes a knob housing, an inner surface of the knob driver is provided with the first cooperating component or the second cooperating component.

In some embodiments, an external surface of the knob body is provided with a first boss, the first cooperating component is provided at the inner surface of the knob housing, the second cooperating component is provided at a proximal end side or a distal end side of the first boss; or the second cooperating component is provided at the inner surface of the knob housing, and the first cooperating component is provided at the proximal end side or the distal end side of the first boss.

In some embodiments, the external surface of the knob body is further provided with a second boss located at a proximal end side of the first boss; the second boss is provided with the first cooperating component or the second cooperating component, and a height of the first cooperating component or the second cooperating component provided at the second boss is lower than a height of the first boss, a distal end of the knob body is cooperated with the first boss.

In some embodiments, the knob assembly further includes a knob cover located at a proximal end of the knob body, a distal end of the knob cover is provided with internal threads, the proximal end of the knob body is provided with external threads cooperated with the internal threads.

In the present disclosure, a circular stapler including the knob assembly is provided.

The knob assembly and the circular stapler has the following advantages.

The present disclosure provides a knob assembly for a circular stapler, wherein the knob assembly includes a knob body and a knob driver, and the knob driver and the knob body are selectively linked with each other. Before the rotating resistance to the knob body reaches the preset resistance value, the knob driver can drive the knob body to rotate together, then the knob body can drive the anvil assembly through the screw rod, to move towards the cartridge along the axial direction of the stapler. When the rotating resistance to the knob body reaches the preset resistance value, as the elastic cooperating component is deformed, the knob driver cannot drive the knob body to rotate further, so the knob assembly is in the failure mode. Therefore, the position of the anvil assembly relative to the cartridge remains unchanged, and the tissues will not be excessively compressed.

BRIEF DESCRIPTION OF THE DRAWINGS

Embodiments of the present disclosure will now be described, by way of example only, with reference to the accompanying schematic drawings. Apparently, the following figures are only exemplary. For the skilled in the art, other figures can also be gotten according to the following figures without creative work.

DETAILED DESCRIPTION

Figure 1:
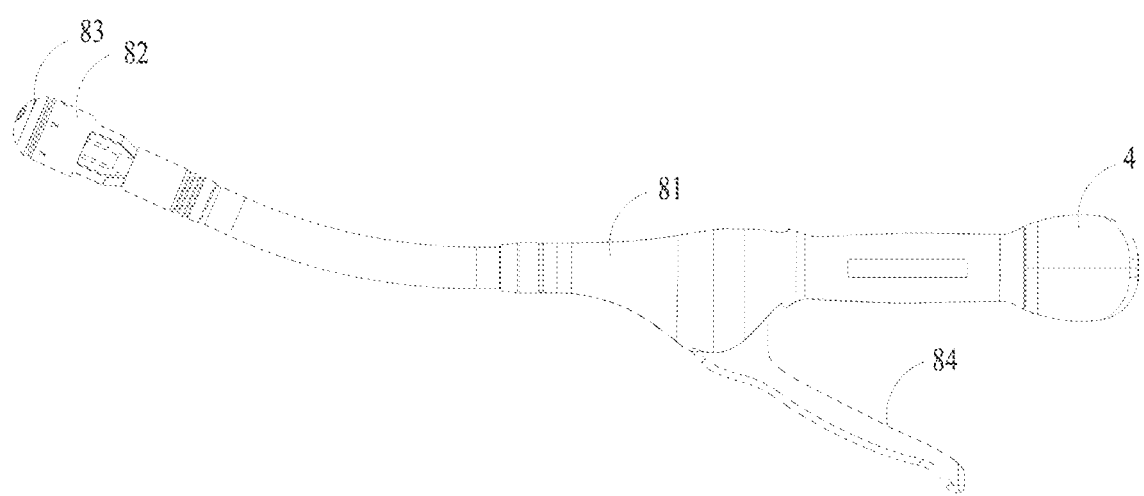
FIG. 1 is a structural schematic view of a stapler according to a first embodiment of the present disclosure.

Embodiments of the present disclosure will now be described, by way of example only, with reference to the accompanying schematic drawings according to embodiments of the present disclosure, to make the objective, technical proposal and advantages clearer. It should understand that the embodiment described are only a part of embodiments of the present disclosure, and are not intended to be a limitation to the protection scope of the present disclosure.

The present disclosure will be described in detail combining the embodiments and the schematic drawings.

To solve the technical problem of the existing technology, the present disclosure provides a knob assembly used for a circular stapler. A screw rod is provided in the stapler. The knob assembly includes a knob driver and a knob body selectively linked with each other. The knob body is sheathed outside the screw rod, and when the knob body rotates, the screw rod is driven to move along an axial direction of the stapler. The knob assembly further includes two cooperating components. One of the cooperating components is provided at the knob driver, and the other one of the cooperating components is provided at the knob body. The two cooperating components include a first cooperating component and a second cooperating component, that is, the first cooperating component is provided at the knob driver, and the second cooperating component is provided at the knob body; or the first cooperating component is provided at the knob body, and the second cooperating component is provided at the knob driver. The present disclosure further provides a circular stapler including the above knob assembly.

The first cooperating component is an elastic cooperating component and has a blocking state and an unblocking state. When the first cooperating component is in the blocking state, the first cooperating component and the second cooperating component are fixedly linked with each other; when the first cooperating component is in the unblocking state, the first cooperating component and the second cooperating component are not fixedly linked with each other;

When the operator rotates the knob driver along a first direction, the knob driver transmits the torque through the two cooperating components. Before the rotating resistance to the knob body reaches the preset resistance value, the first cooperating component is in the blocking state, to block a relative movement between the knob driver and the knob body. Therefore, the knob driver can drive the knob body to rotate together through the two cooperating components, that is, the two cooperating components are fixedly linked with each other. Then the knob body further drives the anvil assembly through the screw rod, to move towards the cartridge assembly along the axial direction of the stapler.

Along with the anvil assembly moving towards the cartridge assembly, when the anvil assembly reaches the appropriate position relative to the cartridge assembly, and the compressing force to the tissues reaches an appropriate preset value, if the operator continues to rotate the knob, the knob body comes to be forced by a rotating resistance blocking the rotation along a first direction, the rotating resistance corresponds to the compressing force to the tissues accommodated between the anvil assembly and the cartridge assembly. At this time, the knob body can only be rotated when the operator applies a rotating force larger than the rotating resistance. That is, after rotating resistance to the knob body reaches the preset resistance value, the mutual force between the first cooperating component and the second cooperating component is larger than a force to overcome the elastic deformation of the elastic cooperating component (the first cooperating component), the first cooperating component is deformed and enters the unblocking state, that is, the first cooperating component no longer blocks the relative movement between the knob driver and the knob body, the knob driver and the knob body are not fixedly linked with each other. At this time, the knob assembly is in the failure mode, the position of the anvil assembly relative to the cartridge assembly remains unchanged, and the tissues will not be excessively compressed.

In the following, the circular stapler and the knob assembly therein will be described in detail combining with the schematic drawings. FIGS. 1-8 are schematic views of the knob assembly according to a first embodiment, wherein, the first cooperating component is provided at the knob driver, and the second cooperating component is provided at the knob body. FIGS. 9-13 are schematic views of the knob assembly according to a second embodiment, wherein, the first cooperating component is provided at the knob body, and the second cooperating component is provided at the knob driver.

FIG. 1 is a schematic view of the stapler according to the first embodiment. The stapler includes an instrument body and an anvil assembly 83, wherein, the instrument body includes a stapler housing 81, a cartridge assembly 82 located at a distal end of the stapler housing 81, a knob assembly located at a proximal end of the stapler housing 81, and a screw rod 6 extending from the proximal end towards the distal end of the stapler. The cartridge assembly 82 includes an annular cartridge and a cutter, the anvil assembly 83 includes an anvil and an anvil shaft, the anvil is connected to a distal end of the screw rod 6 through an anvil shaft. When the knob assembly rotates, the anvil assembly 83 is driven to move through the screw rod 6 and the anvil shaft in sequence, to move away from or towards the cartridge assembly 82.

Alternatively, in another kind of circular stapler, such as the circular stapler for the hemorrhoid operation mentioned above, the anvil assembly 83 is connected to the instrument body directly, the anvil assembly 83 cannot be removed from the instrument body. So, the anvil assembly 83 has no anvil shaft, the anvil is connected to the distal end of the screw rod directly.

As shown in FIGS. 2-8, the knob assembly includes a knob body 1 and a knob driver. In the embodiment, the knob driver is a knob housing 2. When operating the knob assembly, the operator rotates the knob housing 2 directly, but the present disclosure is not limited to this. The knob body 1 is sheathed outside the screw rod 6, and the knob body 1 cooperates with the screw rod 6 through internal threads 13 of the knob body 1. When the knob body 1 rotates along the first direction, the screw rod 6 is driven to move towards the proximal end of the stapler, and further drives the anvil assembly 83 to move towards the cartridge assembly 82. When the knob body 1 rotates along a second direction, the screw rod 6 is driven to move towards the distal end of the stapler, to drive the anvil assembly 83 to move away from the cartridge assembly 82. In the embodiment, the first cooperating component is provided at the knob housing 2, and the second cooperating component is provided on the knob body 1. Wherein, the first cooperating component is an elastic cooperating component, and the first cooperating component has a blocking state and an unblocking state. When the first cooperating component is in the blocking state, the first cooperating component and the second cooperating component are fixedly linked with each other, so the knob housing 2 is relatively fixed to the knob body 1; when the first cooperating component is in the unblocking state, the first cooperating component and the second cooperating component are not fixedly linked with each other, so the knob housing 2 is not fixedly linked with the knob body 1 either.

In the embodiment, the first cooperating component is an elastic sheet 21 having a protruding portion 211. Mounting grooves 22 for the elastic sheet 21 are provided on an inner surface of the knob housing 2, and a first end 212 and a second end 213 of the elastic sheet 21 are correspondingly mounted in the mounting grooves 22 of the knob housing 2. The elastic sheet 21 can be a metal elastic sheet or a plastic elastic sheet, or other kinds of structure that can be elastically deformed under an external force and can return to its initial state when the external force is eliminated. Here only a kind of structure of the elastic cooperating component is described, in other alternative embodiments, the elastic cooperating component can also use the structure including a spring and a movable block or other kinds of structures, which are all included in the protection scope of the present disclosure.

The second cooperating component at least includes one cooperating unit, each cooperating unit can be a bulge or a groove. In the embodiment, the second cooperating component includes a plurality of bulges 11 uniformly distributed at an external surface of the knob body 1. Each bulge 11 has a first side surface 111 and a second side surface 112. When the knob housing 2 rotates along the first direction, the first side surface 111 of the bulge 11 is in contact with the elastic sheet 21; when the knob housing 2 rotates along the second direction, the second side surface 112 of the bulge 11 is in contact with the elastic sheet 21.

When operating the knob assembly, the operator firstly applies an external force to rotate the knob housing 2, the knob housing 2 transmits the external force to the knob body 1 though the two cooperating components. The first cooperating component will give the second cooperating component a rotating force. If the rotating resistance to the knob body 1 at this time is smaller than the preset resistance value, a reacting force of the second cooperating component to the first cooperating component is smaller than the force to overcome the elastic deformation of the elastic sheet 21. The elastic sheet 21 will not be deformed, and the first coopering component is in the blocking state, the knob housing 2 drives the knob body 1 to rotate together through the cooperation of the elastic sheet 21 and the bulge 11. When the operator applies an external force to rotate the knob housing 2, if the rotating resistance to the knob body 1 is equal to or larger than the preset resistance value, the operator continues to apply a larger external force on the knob housing 2. At this time, the reacting force of the bulge 11 to the elastic sheet 21 is larger than the force to overcome the elastic deformation of the elastic sheet 21, the elastic sheet 21 is deformed by the reacting force of the bulge 11 and enters into the unblocking state. Therefore, the bulges 11 and the elastic sheet 21 cannot transmit the external force to the knob body 1. The knob housing 2 cannot be fixedly linked with the knob body 1, the knob housing 2 idles ineffectively, and the knob assembly makes a sound of tick-tick when the bulge 11 and the elastic sheet 21 pass over each other. At this time, the knob assembly is in the failure mode, and the position of the anvil assembly relative to the cartridge assembly remains unchanged, and the tissues will not be excessively compressed. The operator can judge that the anvil assembly 83 is currently moved to the appropriate position when hearing a tick-tick sound or according to the hand feeling during operating the knob housing 2, then the operator can fire the stapler.

In the embodiment, the elastic sheet 21 includes a first guiding surface 214. When the knob housing 2 rotates towards the first direction, the first guiding surface 214 of the elastic sheet 21 is in contact with the bulge 11. The first guiding surface 214 can be an arc surface or an inclined surface. The elastic sheet 21 further includes a second guiding surface 215. When the knob housing 2 rotates towards the second direction, the second guiding surface 215 of the elastic sheet 21 is in contact with the bulge 11. The second guiding surface 215 can be an arc surface or an inclined surface.

Figure 2:
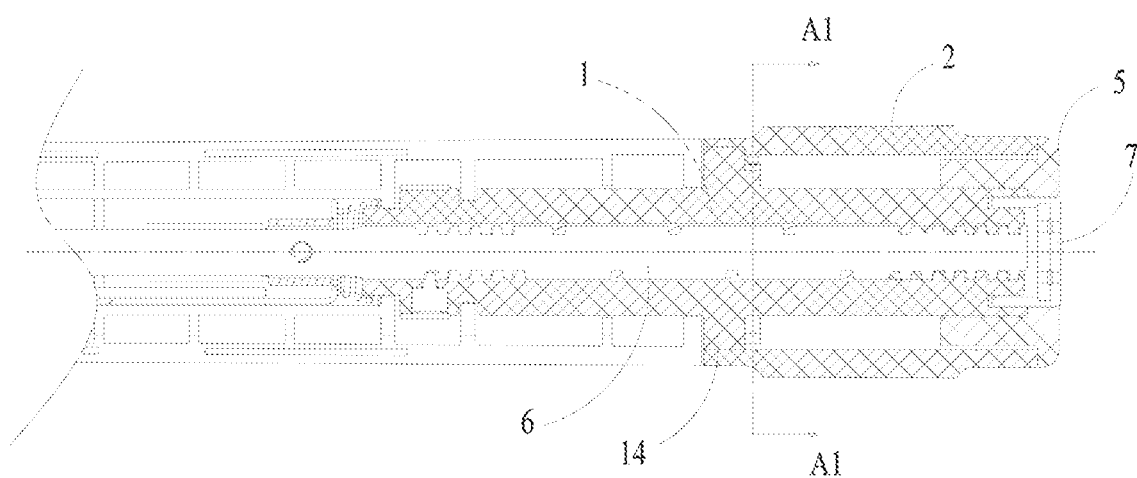
FIG. 2 is a structural schematic view of a knob assembly cooperating with a screw rod according to the first embodiment of the present disclosure.
Figure 3:
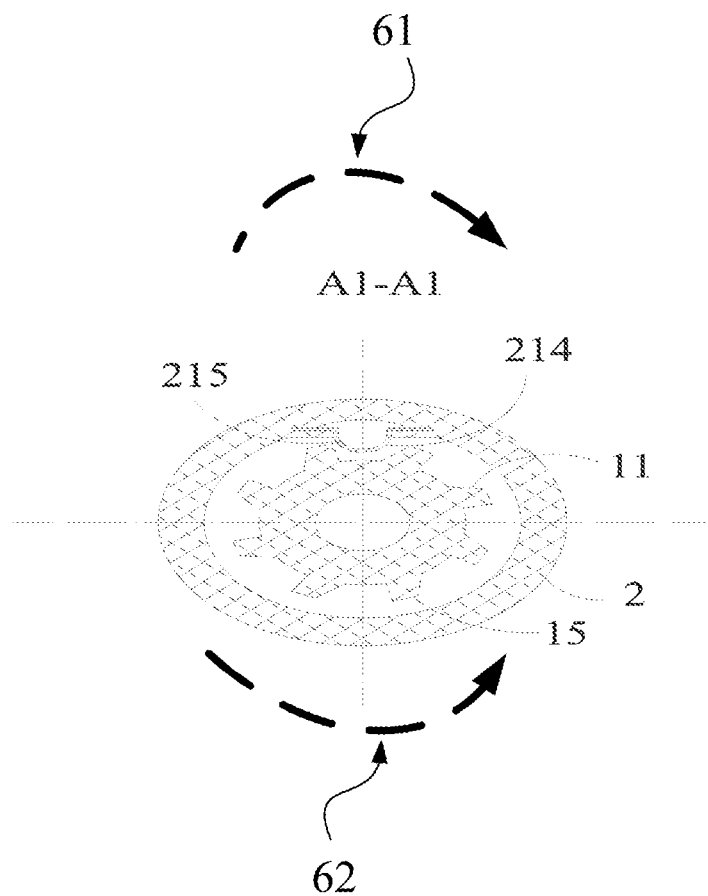
FIG. 3 is a section view along A1-A1 direction of FIG. 2.
Figure 4:
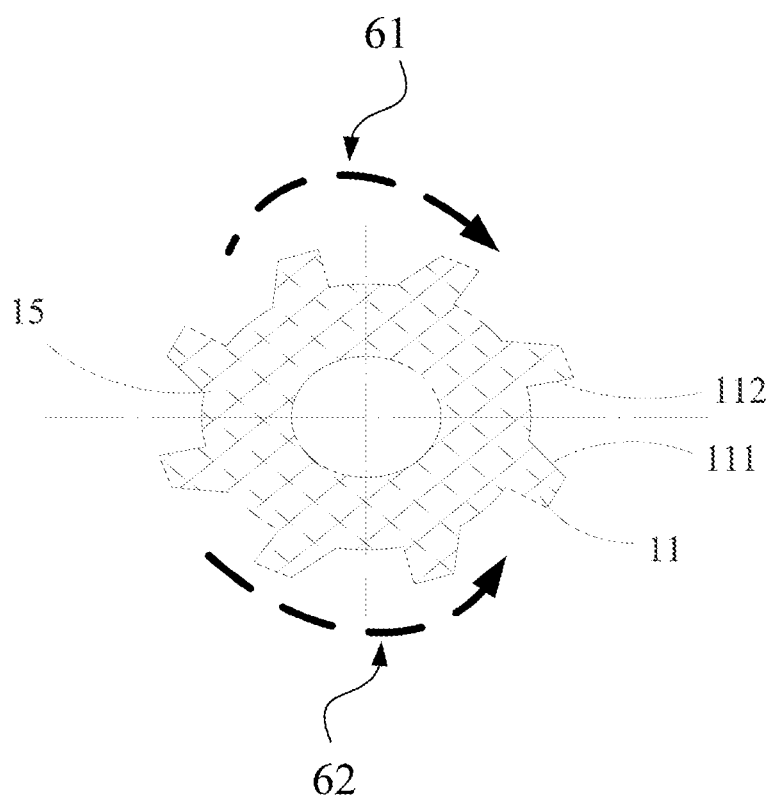
FIG. 4 is a structural schematic view of a second boss according to the first embodiment of the present disclosure.
Figure 5:
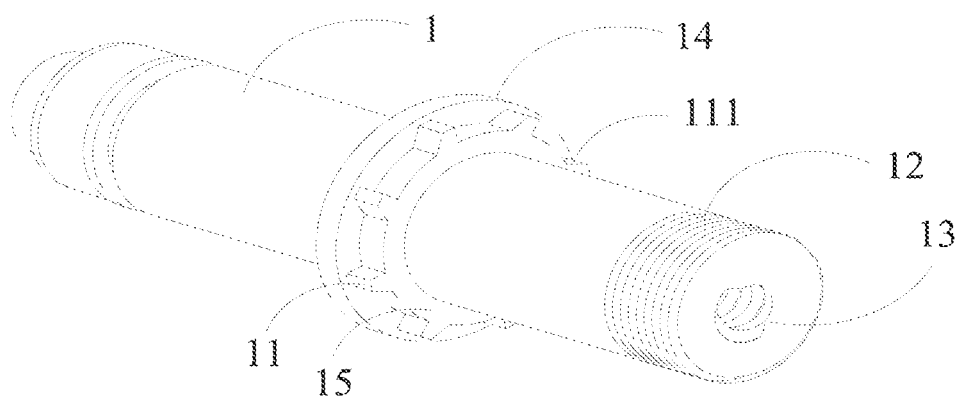
FIG. 5 is a structural schematic view of a knob body according to the first embodiment of the present disclosure.
Figure 6:
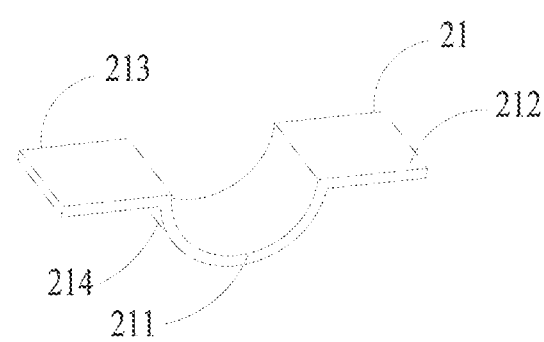
FIG. 6 is a structural schematic view of an elastic sheet according to the first embodiment of the present disclosure.
Figure 7:
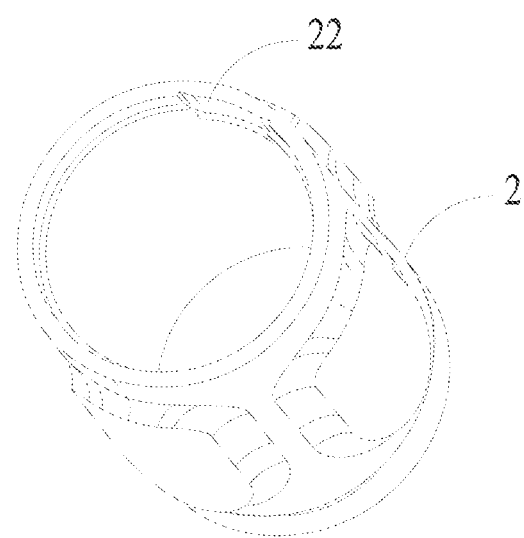
FIG. 7 is a structural schematic view of a knob housing according to the first embodiment of the present disclosure.
Figure 8:
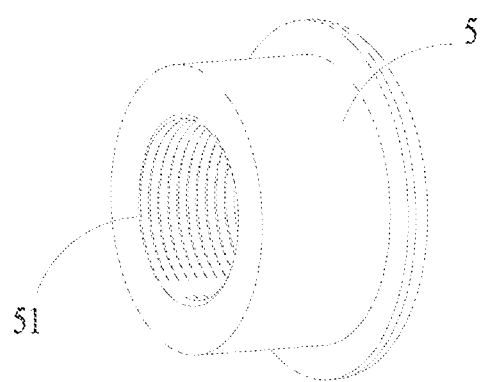
FIG. 8 is a structural schematic view of a knob cover according to the first embodiment of the present disclosure.
Figure 9:
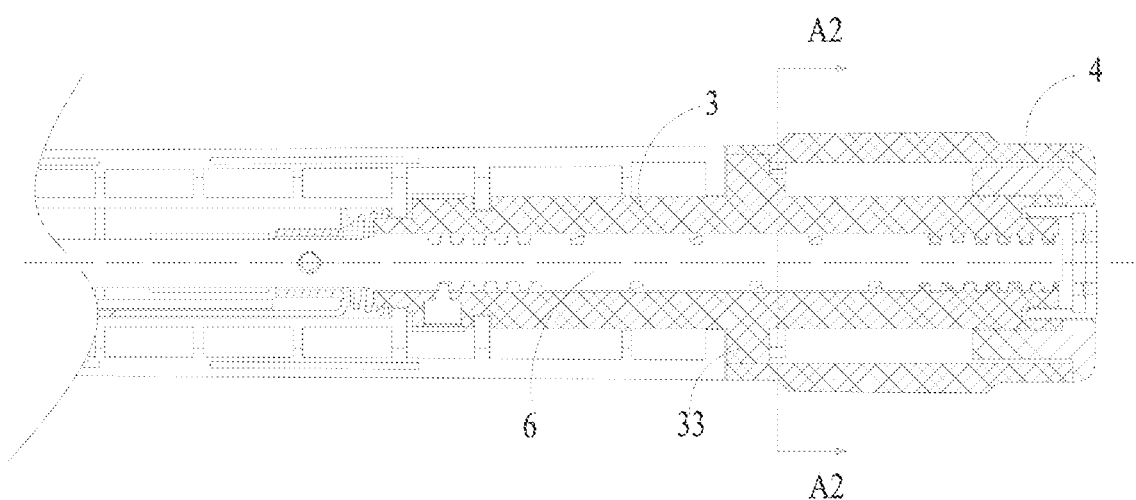
FIG. 9 is a structural schematic view of a knob assembly cooperating with a screw rod according to a second embodiment of the present disclosure.

As shown in FIG. 2, a first boss 14 is provided at the external surface of the knob body 1, and a second boss 15 is provided at a proximal end side of the first boss 14. The bulges 11 are provided at the second boss 15. As shown in FIG. 3 and FIG. 4, the second boss 15 and the plurality of bulges 11 together form a gear disk. Here only a kind of embodiment is described. In other alternative embodiments, there can be only one of the first boss and the second boss, or the second boss 15 can be provided at a distal end side of the first boss 14, etc., which are all included in the protection scope of the present disclosure.

In the embodiment, a height of each bulge 11 at the second boss 15 is lower than a height of the first boss 14. Correspondingly, a distal end of the knob housing 2 is provided with a step surface cooperating with the first boss 14, to limit the movement of the knob housing 2 along the axial direction of the stapler. An inner of a distal end of knob housing 2 is provided with the elastic sheet 21 cooperating with the bulge 11.

Furthermore, a proximal end of the knob assembly is further provided with a knob cover, the knob cover includes a first knob cover 5 and a second knob cover 7. A distal end of the first knob cover 5 is provided with internal threads 51, and a proximal end of the knob body 1 is provided with external threads 12 cooperated with the internal threads 51 of the first knob cover 5. The first knob cover 5 is connected to the proximal end of the knob body 1 through threads connection. The second knob cover 7 can be mounted at a proximal end of the first knob cover 5.

In the viewpoint of FIG. 3 and FIG. 4, the first direction is a clockwise direction 61, and the second direction is an anticlockwise direction 62. As shown in FIG. 3 and FIG. 4, in the embodiment, the first side surface 111 of each bulge 11 inclines towards the first direction, so that when the knob housing 2 rotates clockwise and is not fixedly linked with the knob body 1, the deformed elastic sheet 21 can pass over the bulges 11 easily. The second side surface 112 of each bulge 11 is an approximal vertical surface or the second side surface 112 of each bulge 11 inclines towards the second direction, to prevent the knob housing 2 from rotating towards the second direction when there is no force applied on the knob housing 2, and give the doctor a feedback of operational hand feeling, to indicate the doctor the right rotation direction. Here the second side surface 112 of the bulge 11 being an approximal vertical surface means that the second side surface 112 is basically perpendicular to the external surface of the knob body 1. If the second side surface 112 of the bulge 11 inclines towards the second direction 112, an inclined angle of the second side surface 112 is smaller than an inclined angle of the first side surface 111. With this configuration, it will be harder for the elastic sheet 21 to pass over the bulges 11 when the knob housing 2 rotates along the second direction. Besides, after the knob assembly is rotated to a maximum extent along the first direction, when a contrarotation is needed, the operator can rotate the knob housing 2 along the second direction, to drive the anvil assembly 83 to move away from the cartridge assembly 82. In another alternative embodiment, the first direction can be an anticlockwise direction, and the second direction can be a clockwise direction, then the first side surface 111 of each bulge 11 inclines towards the anticlockwise direction, so that when the knob housing 2 rotates anticlockwise and is not fixedly linked with the knob body 1, the deformed elastic sheet 21 can pass over the bulges 11 easily.

FIGS. 9-13 are schematic views of a knob assembly according to a second embodiment of the present disclosure. The difference between the first embodiment and the second embodiment is, the first cooperating component is provided at the knob body 3, and the second cooperating component is provided at the knob housing 4.

Figure 10:
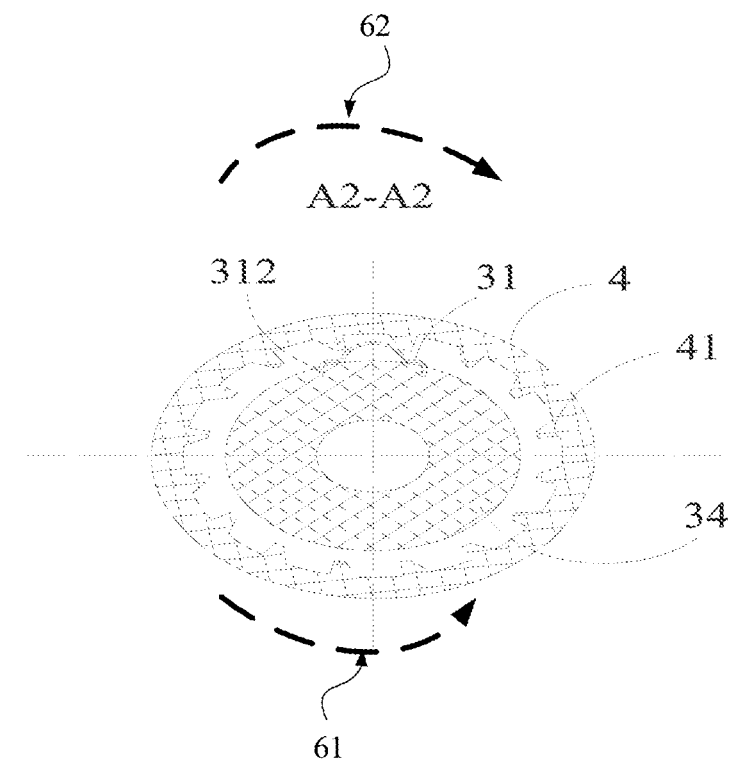
FIG. 10 is a section view along A2-A2 direction of FIG. 9.
Figure 11:
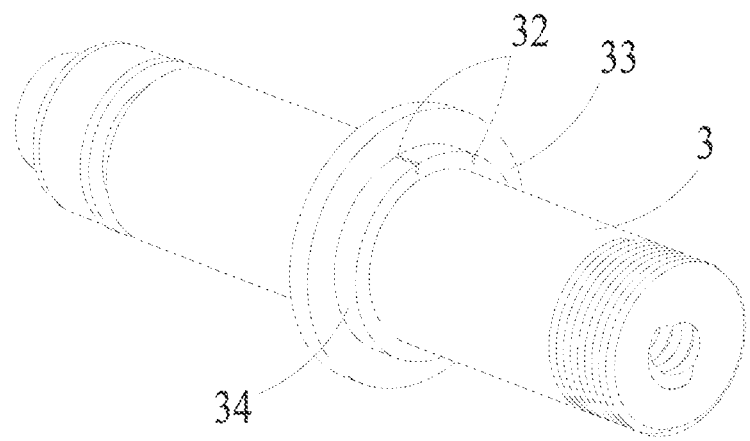
FIG. 11 is a structural schematic view of a knob body according to the second embodiment of the present disclosure.
Figure 12:
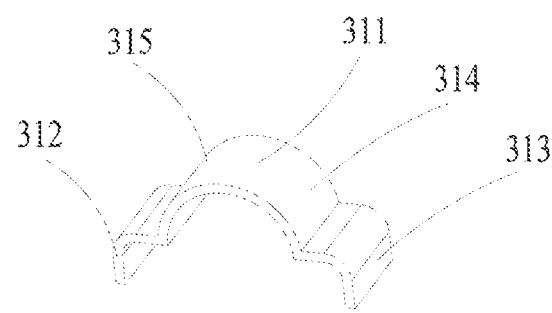
FIG. 12 is a structural schematic view of an elastic sheet according to the second embodiment of the present disclosure.
Figure 13:
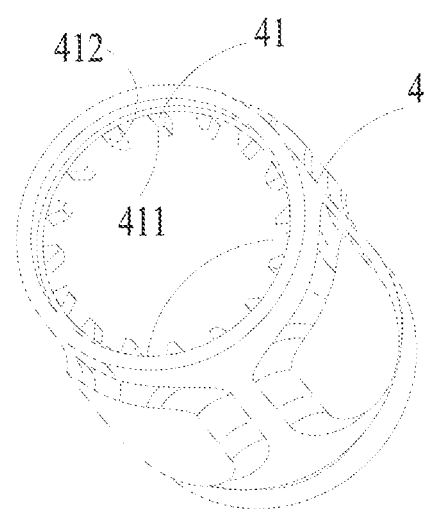
FIG. 13 is a structural schematic view of a knob housing according to the second embodiment of the present disclosure.

In the viewpoint of FIG. 10, the first direction 61 is an anticlockwise direction, and the second direction 62 is a clockwise direction. The first cooperating component is an elastic sheet 31 having a protruding portion 311. The second cooperating component includes a plurality of bulges 41 provided at an inner surface of the knob housing 4. When the knob housing 4 rotates along the first direction, the elastic sheet 31 is in contact with a first side surface 411 of the bulge 41; when the knob housing 4 rotates along the second direction, the elastic sheet 31 is in contact with a second side surface 412 of the bulge 41. Similar to the first embodiment, an inclined angle of the first side surface 411 is larger than an inclined angle of the second side surface 412, so that when the knob housing 4 rotates along the first direction and the rotating resistance to the knob body 3 is larger than the preset resistance value, the elastic sheet 31 can pass over the bulges 41 easily. Besides, the structure ensures that after the knob housing 4 is rotated to a maximum extent along the first direction, the operator can rotate the knob housing 4 along the second direction to rotate the knob body 3 when needed.

Mounting grooves 32 for the elastic sheet 31 is provided on an outer surface of the knob body 3, and two ends 312, 313 of the elastic sheet 31 are correspondingly mounted in the mounting grooves 32 of the knob body 3. The elastic sheet 31 includes a first guiding surface 314 and a second guiding surface 315. When the knob housing 4 rotates along the first direction, the first guiding surface 314 of the elastic sheet 31 is in contact with the first side surface 411 of the bulge 41; when the knob housing 4 rotates along the second direction, the second guiding surface 315 of the elastic sheet 31 is in contact with the second side surface 412 of the bulge 41.

In the embodiment, the knob body 1 is provided with a first boss 33 and a second boss 34, and the second boss 34 is located at a proximal end side of the first boss 33. The first boss 33 acts on a distal end of the knob housing 4 to limit the axial movement of the knob housing 4. The mounting grooves 32 for the elastic sheet 31 is located on the outer surface of the second boss 34. The distal end of the knob housing 4 cooperates with the first boss 33.

The working principle of the stapler having the knob assembly of the second embodiment is similar to the working principle of the stapler having the knob assembly of the first embodiment. When operating the knob assembly, the operator firstly applies an external force to rotate the knob housing 4, the knob housing 4 transmits the external force to the knob body 3 though the two cooperating components. The first cooperating component will give the second cooperating component a driving force intended to rotate the knob body 3. If the resistance to the knob body 3 that resisting the rotation of the knob body is smaller than the preset resistance value, a reacting force of the second cooperating component to the first cooperating component is smaller than the force to overcome the elastic deformation of the elastic sheet 31. The elastic sheet 31 will not be deformed, and the first coopering component is in the blocking state, the knob housing 4 drives the knob body 3 to rotate together through the cooperation of the elastic sheet 31 and the bulges 41. When the operator applies an external force to rotate the knob housing 4, if the rotating resistance to the knob body 3 is equal to or larger than the preset resistance value, the operator continues to apply a larger external force on the knob housing 4. At this time, the reacting force of the bulge 41 to the elastic sheet 31 is larger than the force to overcome the elastic deformation of the elastic sheet 31, the elastic sheet 31 is deformed by the reacting force of the bulges 41, and enters into the unblocking state. Therefore, the bulges 41 and the elastic sheet 31 cannot transmit the external force to the knob body 3. The knob housing 4 cannot be fixedly linked with the knob body 3, the knob housing 4 idles ineffectively, and the knob assembly makes a sound of tick-tick when the bulges 41 and the elastic sheet 31 pass over each other. At this time, the knob assembly is in the failure mode, the position of the anvil assembly 83 relative to the cartridge assembly 82 remains unchanged, and the tissues will not be excessively compressed. The operator can judge that the anvil assembly 83 is currently moved to the appropriate position when hearing a tick-tick sound or according to the hand feeling during operating, then the operator can fire the stapler.

It should be understood that, no matter in the first embodiment, or in the second embodiment, the number of the elastic sheet can be two, or more than two. For example, when there are two elastic sheets, the elastic sheets can be symmetrically located, to enhance the stability of the structure.

The two embodiments of the present disclosure are only exemplary. In other embodiments, some features of the two embodiments can be combined to get a new proposal, or some features can be changed to get a new proposal, which are all included in the protection scope of the present disclosure. For example, the first cooperating component can use a structure including a movable block and a spring cooperated with each other rather than the elastic sheet, the force to overcome the elastic deformation is the elastic force of the spring, the second cooperating component can use grooves as the cooperating units instead of the bulges, and the number and the distribution way of the cooperating units can be changed according to different requirements.

The knob assembly and the circular stapler has the following advantages.

The present disclosure provides a knob assembly for a circular stapler, wherein the knob assembly includes a knob body and a knob driver, and the knob driver and the knob body are selectively linked with each other. Before the rotating resistance to the knob body reaches the preset resistance value, the knob driver can drive the knob body to rotate together, then the knob body can drive the anvil assembly through the screw rod, to move towards the cartridge along the axial direction of the stapler. When the rotating resistance to the knob body reaches the preset resistance value, as the elastic cooperating component is deformed, the knob driver cannot drive the knob body to rotate further, so the knob assembly is in the failure mode. Therefore, the position of the anvil assembly relative to the cartridge remains unchanged, and the tissues will not be excessively compressed.

The above is a detailed description of the present disclosure in connection with the specific preferred embodiments, and the specific embodiments of the present disclosure are not limited to the description. Modifications and substitutions can be made without departing from the spirit and scope of the present disclosure.

What is claimed is:

1. A knob assembly, wherein, the knob assembly is used for a circular stapler, a screw rod is provided in the stapler, and the knob assembly comprises:
    a knob driver;
    a knob body sheathed outside the screw rod, wherein when the knob body rotates, the screw rod is driven to move along an axial direction of the stapler;
    a first cooperating component having a blocking state and an unblocking state, wherein the first cooperating component is an elastic cooperating component;
    a second cooperating component;
    wherein when the first cooperating component is in the blocking state, the first cooperating component and the second cooperating component are fixedly linked with each other, when the first cooperating component is in the unblocking state, the first cooperating component and the second cooperating component are not fixedly linked with each other;
    wherein the first cooperating component is provided at the knob driver, and the second cooperating component is provided at the knob body; or the first cooperating component is provided at the knob body, and the second cooperating component is provided at the knob driver.

2. The knob assembly according to claim 1, wherein, the knob driver is capable of being rotated by an external force; when a rotating resistance to the knob body is larger than a preset resistance value, the first cooperating component is deformed by a force of the second cooperating component, then the second cooperating component passes over the first cooperating component, and the first cooperating component enters the unblocking state.

3. The knob assembly according to claim 1, wherein, the first cooperating component is an elastic sheet having a protruding portion.

4. The knob assembly according to claim 3, wherein, the knob driver or the knob body is provided with mounting grooves for the elastic sheet, two ends of the elastic sheet are correspondingly mounted in the mounting grooves for the elastic sheet.

5. The knob assembly according to claim 3, wherein, the elastic sheet comprises a first guiding surface; when the knob driver rotates towards a first direction, the first guiding surface of the first cooperating component is in contact with the second cooperating component.

6. The knob assembly according to claim 5, wherein, the first guiding surface is an arc surface or an inclined surface.

7. The knob assembly according to claim 5, wherein, the elastic sheet comprises a second guiding surface; when the knob driver rotates towards a second direction, the second guiding surface of the first cooperating component is in contact with the second cooperating component.

8. The knob assembly according to claim 7, wherein, the second guiding surface is an arc surface or an inclined surface.

9. The knob assembly according to claim 1, wherein, the second cooperating component comprises at least one cooperating unit, each cooperating unit is a bulge or a groove.

10. The knob assembly according to claim 9, wherein, each cooperating unit comprises a first side surface inclined towards a first direction; when the knob driver rotates towards a first direction, the first side surface of the cooperating unit is in contact with the first cooperating component.

11. The knob assembly according to claim 10, wherein, each cooperating unit comprises a second side surface; when the knob driver rotates towards a second direction, the second side surface of the cooperating unit is in contact with the first cooperating component.

12. The knob assembly according to claim 11, wherein, the second side surface of the cooperating unit is a vertical surface; or the second side surface of the cooperating unit inclines towards a second direction with an inclined angle smaller than an inclined angle of the first side surface of the cooperating unit.

13. The knob assembly according to claim 1, wherein, the knob driver comprises a knob housing, an inner surface of the knob driver is provided with the first cooperating component or the second cooperating component.

14. The knob assembly according to claim 13, wherein, an external surface of the knob body is provided with a first boss, the first cooperating component is provided at the inner surface of the knob housing, the second cooperating component is provided at a proximal end side or a distal end side of the first boss; or the second cooperating component is provided at the inner surface of the knob housing, and the first cooperating component is provided at the proximal end side or the distal end side of the first boss.

15. The knob assembly according to claim 14, wherein, the external surface of the knob body is further provided with a second boss located at a proximal end side of the first boss;

the second boss is provided with the first cooperating component or the second cooperating component, and a height of the first cooperating component or the second cooperating component provided at the second boss is lower than a height of the first boss, a distal end of the knob body is cooperated with the first boss.

16. The knob assembly according to claim 1, wherein, the knob assembly further comprises a knob cover located at a proximal end of the knob body, a distal end of the knob cover is provided with internal threads, the proximal end of the knob body is provided with external threads cooperated with the internal threads of the knob cover.

17. A circular stapler, comprising the knob assembly according to claim 1.

* * * * *